United States Patent [19]

Devries et al.

[11] Patent Number: 4,704,487

[45] Date of Patent: Nov. 3, 1987

[54] CONVERSIONS OF LOW MOLECULAR WEIGHT HYDROCARBONS TO HIGHER MOLECULAR WEIGHT HYDROCARBONS USING A METAL COMPOUND-CONTAINING CATALYST (IV-B)

[75] Inventors: Louis Devries, Greenbrae; Porter R. Ryason, Santa Rosa, both of Calif.

[73] Assignee: Chevron Research Company, San Francisco, Calif.

[21] Appl. No.: 879,859

[22] Filed: Jun. 27, 1986

Related U.S. Application Data

[63] Continuation-in-part of Ser. No. 547,699, Oct. 31, 1983, Pat. No. 4,599,474.

[51] Int. Cl.$^4$ .............................................. C07C 2/00
[52] U.S. Cl. .................................. 585/417; 585/500; 585/541; 585/654; 585/661; 585/700; 585/943
[58] Field of Search ............... 585/415, 654, 700, 943, 585/661, 500, 417, 541

[56] References Cited

U.S. PATENT DOCUMENTS

| | | | |
|---|---|---|---|
| 4,205,194 | 5/1980 | Mitchell, III et al. | 585/500 |
| 4,239,658 | 12/1980 | Mitchell, III et al. | 585/500 |
| 4,567,311 | 1/1986 | Devries et al. | 585/500 |

OTHER PUBLICATIONS

Trelant Fong, "Catalytic Pyrolysis of Methane", J. Chinese Chem. Sec., 29, 265–273, (1981).
Keller and Bhasin, "Synthesis of Ethylene via Oxidative Coupling of Methane", J. of Catalysis 73, 9–19, (1982).

*Primary Examiner*—William R. Dixon, Jr.
*Assistant Examiner*—Cynthia A. Prezlock
*Attorney, Agent, or Firm*—S. R. LaPaglia; R. C. Gaffney; J. J. DeYoung

[57] ABSTRACT

Disclosed is a catalytic process for the production of higher molecular weight hydrocarbons from lower molecular weight hydrocarbons. More particularly, disclosed is a catalytic process for the conversion of methane to $C_2+$ hydrocarbons, particularly hydrocarbons rich in ethylene or benzene, or both. The process utilizes a metal-containing catalyst, high reaction temperature of greater than 1000° C., and a high gas hourly space velocity of greater than 3200 hr$^{-1}$.

15 Claims, No Drawings

CONVERSIONS OF LOW MOLECULAR WEIGHT HYDROCARBONS TO HIGHER MOLECULAR WEIGHT HYDROCARBONS USING A METAL COMPOUND-CONTAINING CATALYST (IV-B)

CROSS REFERENCE TO RELATED APPLICATIONS

This application is a continuation-in-part of Ser. No. 547,699, now U.S. Pat. No. 4,599,474 filed Oct. 31, 1983, the entire disclosure of which is incorporated herein by reference.

FIELD OF THE INVENTION

The present invention relates to a catalytic process for the production of higher molecular weight hydrocarbons from lower molecular weight hydrocarbons. In particular the process of the present invention utilizes a metal-compound containing catalyst under $C_2+$ hydrocarbon synthesis conditions such that at least 15 mole percent of the lower molecular weight hydrocarbons in the feed gas are converted to higher molecular weight hydrocarbons, said conditions including a temperature of greater than 1000° C. and a gas hourly space velocity of greater than 3200 $hr^{-1}$. More particularly, the present invention relates to the conversion of methane using a Group IV-B metal compound containing catalyst.

BACKGROUND OF THE INVENTION AND PRIOR ART

It is the business of many refineries and chemical plants to obtain, process and upgrade relatively low value hydrocarbons to more valuable feeds, or chemical raw materials. For example, methane, the simplest of the saturated hydrocarbons, is often available in rather large quantities either as an undesirable by product in admixture with other more valuable higher molecular weight hydrocarbons, or as a component of an off gas from a process unit, or units. Though methane is useful in some chemical reactions, e.g., as a reactant in the commercial production of methanol and formaldehyde, it is not as useful a chemical raw material as most of the higher molecular weight hydrocarbons. For this reason process streams which contain methane are usually burned as fuel.

Methane is also the principal component of natural gas, which is composed of an admixture of normally gaseous hydrocarbons ranging $C_4$ and lighter and consists principally of methane admixed with ethane, propane, butane and other saturated, and some unsaturated hydrocarbons. Natural gas is produced in considerable quantities in oil and gas fields, often at remote locations and in difficult terrains, e.g., offshore sites, arctic sites, swamps, deserts and the like. Under such circumstances the natural gas is often flared while the oil is recovered, or the gas is shut in, if the field is too remote for the gas to be recovered on a commercial basis. The construction of pipelines to carry the gas is often not economical, due particularly to the costs of connecting numerous well sites with a main line. Transport of natural gas under such circumstances is also uneconomical because methane at atmospheric pressure boils at −258° F. and transportation economics dictate that the gas be liquefiable at substantially atmospheric pressures to reduce its volume. Even though natural gas contains components higher boiling than methane, and such mixtures can be liquefied at somewhat higher temperatures than pure methane, the temperatures required for condensation of the admixture is nonetheless too low for natural gas to be liquefied and shipped economically. Under these circumstances the natural gas, or methane, is not even of sufficient value for use as fuel, and it is wasted.

The thought of utilizing methane from these sources, particularly avoiding the tremendous and absolute waste of a natural resource in this manner, has challenged many minds; but has produced few solutions. It is highly desirable to convert methane to hydrocarbons of higher molecular weight (hereinafter, $C_2+$) than methane, particularly admixtures of $C_2+$ hydrocarbon products which can be economically liquefied at remote sites; especially admixtures of $C_2+$ hydrocarbons rich in ethylene or benzene, or both. Ethylene and benzene are known to be particularly valuable chemical raw materials for use in the petroleum, petrochemical, pharmaceutical, plastics and heavy chemicals industries. Ethylene is thus useful for the production of ethyl and ethylene compounds including ethyl alcohol, ethyl ethers, ethylbenzene, styrene, polyethylbenzenes ethylene oxide, ethylene dichloride, ethylene dibromide, acetic acid, oligomers and polymers and the like. Benzene is useful in the production of ethylbenzene, styrene, and numerous other alkyl aromatics which are suitable as chemical and pharmaceutical intermediates, or suitable in themselves as end products, e.g., as solvents or high octane gasoline components.

It has been long known that methane, and natural gas could be pyrolytically converted to $C_2+$ hydrocarbons. For example, methane or natural gas passed through a porcelain tube at moderate red heat will produce ethylene and its more condensed homologues such as propylene, as well as small amounts of acetylene and ethane. Methane and natural gas have also been pyrolytically converted to benzene, the benzene usually appearing in measurable quantities at temperatures above about 1650° F. (899° C.), and perhaps in quantities as high as 6–10 wt. % at 2200° F. to 2375° F., (1204° to 1302° C.) or higher. Acetylene and benzene in admixture with other hydrocarbons, have been produced from methane and natural gas in arc processes, cracking processes, or partial combustion processes at temperatures ranging above about 2775° F. (1524° C.). Heat for such reactions has been supplied from various sources including electrically heated tubes, electric resistance elements, and spark or arc electric discharges. These processes characteristically require considerable heat energy which, most often, is obtained from combustion of the by-product gases. The extreme temperatures coupled with the low yields of higher molecular weight hydrocarbons have made the operation of such processes uneconomical.

High temperature, noncatalytic, thermal pyrolysis processes involving the conversion of methane in the presence of ethane and other hydrocarbons are well known in the art. Representative articles include: Roczniki Chemi, An. Soc. Chim. Polonorum, 51, 1183 (1977), "The Influence of Ethane on Thermal Decomposition of Methane Studied By The Radio Chromatographic Pulse Technique"; J. Soc. Chem. Ind. (Trans. and Comm.) 1939,58, 323–7; and J. Chin. Chem. Soc. (Taipei) 1983, 30(3), 179–83.

Addition of hydrogen to pyrolysis reaction mixtures is well known, see for example, pp 84–85 in "Pyrolysis Theory and Industrial Practice", L. F. Albright, B. L. Crynes and W. H. Corcoran (Ed.), Academic Press (1983).

Partial oxidation processes of converting methane to $C_{2+}$ hydrocarbons are well known. In these processes, hydrogen must be removed either as water, molecular hydrogen or other hydrogen-containing species. Likewise, any other polymerization mechanism wherein methane is converted to $C_{2+}$ hydrocarbon products requires a tremendous amount of energy, most often supplied as heat, to provide the driving force for the reactions. In the past the molecular hydrogen liberated by the reaction has often been separated and burned to provide the necessary process heat. This route has proven an abomination to the production of $C_{2+}$ hydrocarbons, but alternate reaction pathways have appeared little better, if any, for these have resulted in the production of large quantities of the higher, less useful hydrogen deficient polymeric materials such as coke, and highly oxidized products such as carbon dioxide and water.

Typical of low temperature prior art processes are those disclosed in U.S. Pat. Nos. 4,239,658, 4,205,194 and 4,172,180 which use a regenerable catalyst-reagent. U.S. Pat. No. 4,239,658, for example, teaches a process for the conversion of methane to higher molecular weight hydrocarbons. In the process, a three component catalyst-reagent is utilized which comprises a mixture of various metals and metal oxides, particularly a Group VIII noble metal, nickel or a Group VI-B noble metal, a Group VI-B metal oxide and a Group II-A metal. The patent teaches process temperatures from about 1150° to 1600° F. (621° to 871° C.), preferably 1250° F. to about 1350° F. (677° to 732° C.).

It has also been reported in Science 153, 1393, (1966), "High Temperature Synthesis of Aromatic Hydrocarbons From Methane", that aromatic hydrocarbons can be prepared from methane by contact with silica at 1000° C. (1832° F.). The yield of hydrocarbons was in the range of 4.8 to 7.2 percent based on the methane used in a single pass at a space velocity of 1224 $hr^{-1}$.

In the J. Chinese Chem. Soc., Volume 29, pages 263-273 (1981), it is reported that methane can be converted to $C_{2+}$ hydrocarbons at temperatures of 800° to 1130° C. and space velocities of 3100 $hr^{-1}$ or less using a metal oxide catalyst. However, the total conversion of methane, at best, is 7.5 mole percent using a thorium oxide catalyst.

Franz Fischer, reports in an article entitled: "The Synthesis of Benzol Hydrocarbons From Methane At Ordinary Pressure and Without Catalyst" (Brennstoff-Chemie, Vol. 9, pp 309-316, 1928) that methane is converted to benzol hydrocarbons by passing methane through a hot tube. In carrying out this work Fischer tested many substances for catalytic activity at temperatures ranging from 650° to 1150° C. and at high flow rates and concluded that the substances tested were not catalytic and not necessary. Among the substances tested were elemental iron, copper, tungsten, molybdenum, tin and carbon; and the compounds potassium hydroxide and silica gel.

SUMMARY OF THE INVENTION

A process for the production of higher molecular weight hydrocarbons from lower molecular hydrocarbons comprising the steps of:

(a) introducing into a reaction zone a lower molecular weight hydrocarbon-containing gas and contacting said gas in said zone with a metal compound-containing catalyst under $C_{2+}$ hydrocarbon synthesis conditions such that at least 15 mole percent of the lower molecular weight hydrocarbons in said gas are converted to higher molecular weight hydrocarbons, said conditions including a temperature of greater than 1000° C. and a gas hourly space velocity of greater than 3200 $hr^{-1}$;

(b) withdrawing from said reaction zone a higher molecular weight hydrocarbon-containing stream.

The process of the present invention affords high conversions of 19 mole percent or more of the lower molecular weight hydrocarbons with high selectivity, that is, 80 mole percent or more of the reaction products comprise higher molecular weight hydrocarbons.

DETAILED DESCRIPTION OF THE INVENTION AND PREFERRED EMBODIMENTS

It is a primary object of the present invention to provide an improved process for the conversion of low molecular weight hydrocarbons to higher molecular weight hydrocarbons with a high conversion of the lower molecular hydrocarbons and high selectivity in the conversion to higher molecular weight hydrocarbons.

It is an essential feature and critical to obtaining the above objects that the process of the present invention is carried out under critical reaction conditions. These critical conditions include the use of a metal compound-containing catalyst, a temperature of at least 1000° C. and a gas hourly space velocity of at least 3200 $hr^{-1}$.

It has been surprisingly found that by using the high contact temperatures of the present invention coupled with the high space velocity, the metal compound-containing catalyst used in the present invention do not rapidly foul and the yield of less valuable coke is low while the yield of higher molecular weight hydrocarbons is high.

As used in the present invention the word "metal" refers to all those elements of the periodic table which are not non-metals. "Non-metals" for the purpose of the present invention refers to those elements having atomic numbers 1, 2, 5 through 10, 14 through 18, 33 through 36, 52 through 54, 85 and 86.

As used in the present invention the phrase "lower molecular weight hydrocarbons" means hydrocarbons containing at least one or more carbon atoms, i.e., methane, ethane, propane, etc. Also as used in the present invention, the phrase "higher molecular weight hydrocarbons" means hydrocarbons containing two or more carbon atoms and at least one carbon atom more than the lower molecular weight feedstock.

As used herein the phrase "$C_{2+}$ hydrocarbon synthesis conditions" refers to the selection of feedstock, reaction temperature, space velocity and catalyst described hereafter such that higher molecular weight hydrocarbons are produced in the process with yields as described hereafter. Other process parameters necessary to maintain $C_{2+}$ hydrocarbon synthesis conditions, such as the selection of particular types of reaction vessels, etc., is readily determined by any person skilled in the art.

The word "catalyst" is used in the present invention to mean a substance which strongly affects the rate of a chemical reaction but which itself undergoes no chemical change although it may be altered physically by chemically absorbed molecules of the reactants and reaction products.

As used in the present invention the phrase "continuous catalytic process" means a process in which feedstock and products are simultaneously fed to and removed from a reaction zone containing a catalyst.

As used in the present invention the words "light aromatics" refers to single ring aromatic hydrocarbons, for example, benzene, toluene, xylenes, and so forth.

The Feedstock and Products

Generally, the feedstock lower molecular weight hydrocarbon of the present invention will comprise methane or natural gas containing $C_1$ to $C_4$ hydrocarbons. The product higher molecular weight hydrocarbons will comprise $C_2+$ hydrocarbons, particularly mixtures of $C_2+$ hydrocarbons which can be economically liquefied. Preferably, the higher molecular weight hydrocarbon product streams will be rich in ethylene or aromatics such as benzene, or both.

The process of the present invention affords high conversions of the lower molecular weight hydrocarbons with high selectivity to higher molecular weight hydrocarbons. More particularly, as measured by the disappearance of the lower molecular weight hydrocarbons, the process of the present invention affords conversions of 19 mole percent or more of the lower molecular weight hydrocarbons, and preferably, the conversions are greater than 25 mole percent and more preferably greater than 40 mole percent. The carbon-containing reaction products comprise 80 mole percent or more higher molecular weight hydrocarbons, preferably, greater than 90 mole percent. Based on the feed, at least 15 mole percent, and preferably at least 20 mole percent, and more preferably at least 40 mole percent of the lower molecular weight hydrocarbons are converted to higher molecular weight hydrocarbons which is referred to herein as selectivity.

Process Conditions

It is critical to the process of the present invention that a high temperature greater than 1000° C. is maintained in the reaction zone along with a high gas hourly space velocity of greater than 3200 $hr^{-1}$. Preferably, the temperature will be greater than 1100° C. with a space velocity greater than 6000 $hr^{-1}$. Still more preferably the temperature is greater than 1150° C. with a space velocity greater than 9000 $hr^{-1}$ Generally, the temperature will be in the range of 1001° to 1300° C. while the gas hourly space velocity is in the range 3200 to 360,000 $hr^{-1}$. Preferably, the temperature is in the range 1100° to 1200° C. with a gas hourly space velocity of 6,000 to 36,000 $hr^{-1}$. More preferably the temperature is in the range 1140° to 1175° C. with a gas hourly space velocity in the range of 9,000 to 18,000 $hr^{-1}$. Generally, high temperatures are used with high space velocities and low temperatures are used with low space velocities.

The process can be operated at sub-atmospheric, atmospheric, or supra atmospheric pressure to react and form the higher molecular weight $C_2+$ hydrocarbons. It is preferred to operate at or near atmospheric pressure or within about 15 psi of atmospheric pressure.

The Catalysts

The lower molecular weight hydrocarbons are introduced into a reaction zone containing a suitable metal compound-containing catalyst.

A wide range of metal compound-containing catalysts and catalyst supports may be used in the present invention. Many commercially available catalysts which have been used in different processes are suitable for use in the process of the present invention. The word "catalyst" is used in the present invention to mean a substance which strongly affects the rate of a chemical reaction but which itself undergoes no chemical change although it may be altered physically by chemically absorbed molecules of the reactants and reaction products. It is also understood that the catalyst of the present invention may be formed in situ. For example, in the present invention when an oxide, nitride, or carbide metal catalyst is initially charged to the reactor, the oxide and nitride may be converted in situ to the carbide which then functions as the catalytic species.

Metal compound-containing catalysts for use in the present invention will provide conversion of the lower molecular weight hydrocarbons of at least 19% and will maintain this conversion for at least 3 hours under the temperature and space velocity conditions previously discussed. Preferred catalysts of the present invention will provide conversions of 30% or more of the lower molecular weight feed and remain active for 3 hours or more.

Representative metal compound-containing catalysts are refractory materials and include the compounds of the Group I-A, II-A, III-A, IV-B or actinide series metals. Representative compounds include the carbide, nitride, boride or oxide of a Group I-A, II-A, III-A, IV-B or actinide series metal, used alone or in combination.

The catalyst must be thermally stable under the operating condition in the reaction zones and are preferably particulate in form. The carbides of the Groups I-A, II-A, III-A, IV-B and actinide series metals are particularly preferred because it is believed that the carbide metal compound-containing catalyst are the most stable under the severe reaction conditions of the present invention. Preferably, the catalyst can also be regenerated by the periodic burning-off of any undesirable deposits such as coke. The regeneration of catalyst by the burning off coke is well known in the catalyst and petroleum processing art.

Representative Group I-A metal compound-containing catalyst include the carbide, nitride, boride, oxide of lithium, sodium, potassium, rubidium, and cesium. Most preferred among the Group I-A metals is lithium.

Representative Group II-A metal compound-containing catalysts include the carbide, nitride, boride, or oxide of beryllium, magnesium, calcium, strontium, barium, and radium. Most preferred among the Group II-A metals is calcium.

Representative Group III-A metal compound-containing catalysts include the carbide, nitride, boride, or oxide of aluminum, scandium, yttrium, lanthanum, and actinium. Most preferred among the Group III-A metals is aluminum.

Representative Group IV-B metal compound-containing catalysts include the carbide, nitride, boride, or oxide of titanium, zirconium, and hafnium. Most preferred among the Group IV-B metals is zirconium.

Representative actinide series metal compound-containing catalysts include the carbide, nitride, boride, or oxide of thorium and uranium. Most preferred among the actinide series metals is thorium.

Catalysts useful in the present invention may be used with and without catalyst supports. However, it is generally preferred to use a catalyst support such as the well known aluminas.

The catalysts useful in the present invention may have a wide range of surface areas as measured by the BET method using krypton [Jour. Am. Chem. Soc., vol. 60, pp 309 (1938)]. Low surface areas are preferred. Generally, the catalyst will have a surface area in the range 0.1 to 10 m²/gram, preferably in the range 0.2 to 2.0 m²/gram.

The reaction-zone catalyst system can be either of the fixed bed type or fluid bed type and the lower molecular weight hydrocarbons can be introduced into the top or bottom of the reaction zone with the product stream removed from either the top or bottom. Preferably, a fixed bed catalyst system is used and the feed stream is introduced into the top of the reaction zone and product is withdrawn from the bottom.

A particularly preferred catalyst for use in the present invention is thorium oxide on alumina.

The advantages of the present invention will be readily apparent from a consideration of the following examples.

EXAMPLES

The examples illustrating the invention were carried out as follows:

The apparatus comprises a vertical reactor tube made of high purity alumina of $\frac{3}{8}''$ O.D. and $\frac{1}{4}''$ I.D. This tube is 24" long, the central 12" of which is surrounded by a high temperature electric furnace (Marshall Model 1134). The heated section of the tube is packed with the test catalyst. A small piece of close fitting alumina honeycomb, or monolith, at the bottom of the bed supports the catalyst. An "O"-ring sealed closure at the top of the reactor tube connects it to a gas flow system, which permits either argon or methane to be passed into the reactor at a measured rate. Gas flows into the reactor are measured with pre-calibrated flowmeters. Gas exiting from the reactor is first passed through a trap packed with dry stainless steel "saddles" (distillation column packing), then through a tube fitted with a rubber septum. Gas samples are taken through the septum with a syringe. Off gas exits the system through a "U"-tube partially filled with oil. Bubbles passing through the oil provide a visual indicator of the gas flow.

In operation, the central section of the reactor tube is packed with the catalyst to be tested. The catalyst particles range in size from 8 mesh to 12 mesh. About 10 cm³ of catalyst is charged to the reactor. The reactor is then placed in the cold furnace, and the necessary input and output connections are made. A slow flow of about 15 to 20 ml/min. of argon is continuously passed through the reactor, which is then brought to the desired temperature over a period of about 150 min. Temperatures reported in Table I are measured by a thermocouple mounted in the furnace wall. Calibration curves, previously developed from a thermocouple in the catalyst bed and compared to the furnace wall thermocouple, are used to determine the reaction temperatures reported in Table I.

Once the reactor tube is at the desired temperature, argon flow is stopped and methane flow is started at the predetermined flow rate. Space velocities are calculated on the basis of the temperature, pressure, methane flow rate into the reactor and on the catalyst bed dimensions. On each run, the reaction is allowed to level out for 15 to 20 minutes before the first analytic sample is withdrawn through the septum. Two samples are taken each time, using one ml gas-tight syringes. Aliquots of these samples (0.25 ml) are separately injected into a gas chromatograph packed with Poropak Q. Analysis is made for hydrogen, methane, and light hydrocarbons having less than 5 atoms of carbon. Other aliquots of the same samples are injected into another gas chromatograph column packed with Bentone 1200. This analysis is made for aromatics, that is, benzene, toluene, and the xylenes. Those aromatic compounds having more than eight carbon atoms are calculated as heavy hydrocarbons in this application. Calculation of the yield and conversion values of Table I from the gas analysis data only is as follows: First, the reaction is assumed to be given by the general expression:

$$CH_4 \rightarrow \beta C + \gamma ``CH'' + (2\beta + 1.5\gamma) H_2$$

wherein "CH" represents the aromatics, C is coke plus higher hydrocarbons called tar/coke in Table I and $\beta$ and $\gamma$ are the number of moles of tar/coke and aromatics, respectively. Then, for one mole of methane fed to the reaction zone, $\alpha$ is the fraction that reacts according to the above equation and $$\alpha = \frac{1 - X_{CH_4}}{1 + (2\beta + 1.5\gamma - 1)X_{CH_4}}$$

wherein $X_{CH_4}$ is the mole fraction of methane in the product gas stream. Finally, an iterative procedure is used to calculate $\beta$ and $\gamma$ based on the gas analysis results.

Table I below gives the details of runs made in accordance with the above description. The table gives the catalyst composition, the space velocity, temperature, and results of runs made on the conversion of methane to $C_2+$ hydrocarbons.

The apparatus and procedures used for obtaining the data in Table II was substantially the same as described above for Table I with the following exceptions:

(1) A large diameter reactor tube ($\frac{3}{4}''$ O.D.$\times\frac{1}{2}''$ I.D.) was used. A central thermowell was inserted in the reactor. The temperature of the catalyst bed was measured at its midpoint, using a platinum/platinum - 10% rhodium thermocouple.

(2) The measurement of coke for data in Table II was carried out as follows: Upon completion of a run to determine catalyst activity and selectivity, the feed was replaced by argon. Air was then added to the argon flow to an extent of 20% by volume. In the meantime, the trapping and sampling system at the reactor exit had been replaced by a CO converter and Ascarite traps to permit trapping and sampling system at the reactor exit had been replaced by a CO converter and Ascarite traps to permit estimation of $CO_2$ formed by reaction of oxygen in the air/argon mixture with coke on the catalyst. Dilute air was used until the temperature maximum, produced by the exothermic coke/oxygen reaction, was past. Then the argon flow was terminated, and 100% air was used at a flow rate equal to the feed flow to assure similar mass transport conditions. By these means, complete combustion of the coke on catalyst was obtained. Weighing the Ascarite absorption tube before and after use afforded the weight of $CO_2$ absorbed, from which the carbon content of the catalyst was readily calculated. Appropriate tests were performed to determine that the CO converter was functioning, and that carbon combustion was complete;

(3) In the calculation of aromatics, heavy hydrocarbons, and coke for the data in Table II, it was assumed that the carbon atoms from converted methane, and the carbon atoms from converted ethane, were uniformly distributed among all the products. Thus, the proportion of carbon atoms in benzene that resulted from methane conversion was the carbon atoms in total product benzene times the fraction $$\frac{\text{(carbon atoms from converted methane)}}{\text{(carbon atoms from converted methane + carbon atoms from converted ethane)}}.$$

Calculation of moles or weight of benzene formed was then straight forward, from the stoichiometric relationships. Similarly calculations were made for the other aromatic compounds and for coke. Finally, heavy hydrocarbon was calculated as the difference: carbon atoms from converted methane minus (carbon atoms in the light aromatics from converted methane plus carbon atoms in coke from converted methane). This difference was multiplied by 13.02 to obtain the weight of heavy hydrocarbon. Assuming a molecular weight of 13.02 corresponds to an assumption that the heavy hydrocarbons have a molecular formula of (CH)x. This is correct to within a few percent. Gas chromatographic analysis of the heavy hydrocarbon collected in the traps showed that about 95% of the heavy hydrocarbon was useful product;

(4) In Table II, the % yield was calculated as follows:

$$\% \text{ Yield} = \frac{\text{(Wt of Useful Products from CH}_4\text{)} \times 100}{\text{Wt of Methane Converted}}$$

Useful products include (1) the aromatics (benzene, toluene and the xylenes) and (2) the heavy hydrocarbons (polynuclear aromatic hydrocarbons containing 4 and fewer fused rings).

It was assumed that the two to four carbon hydrocarbons formed as products were being recycled as feed to the process. The 5% ethane in the feed used in the experiments recorded in Table II simulated this situation. Thus the 5% ethane in the feed essentially corresponds to the two to four carbon hydrocarbons content of the process feed at steady state operation in a reactor in which these products are recycled to the feed.

TABLE I

| | Reaction Conditions | | | Conv. mole % of $CH_4$ fed | Results Fraction of carbon converted, appearing as | | |
|---|---|---|---|---|---|---|---|
| Run No. | Catalyst | Temp. °C. | Sv hr$^{-1}$ | | Light Hydrocarbons | Aromatics | Tar/Coke |
| 1 | A | 1130 | 3600 | 19 | 0.30 | 0.70 | 0 |
| 2 | B | 1150 | 9000 | 24 | 0.38 | 0.47 | 0.15 |
| 3 | C | 1190 | 18000 | 21 | 0.48 | 0.45 | 0.07 |
| 4 | D | 1170 | 12000 | 24 | 0.36 | 0.45 | 0.19 |
| 5 | E | 1170 | 9000 | 43 | 0.19 | 0.28 | 0.53 |
| 6 | E | 1190 | 18000 | 27 | 0.34 | 0.42 | 0.76 |
| 7 | F | 1170 | 18000 | 22 | 0.38 | 0.52 | 0.10 |
| 8 | G | 1170 | 18000 | 35 | 0.19 | 0.22 | 0.59 |
| 9 | H | 1130 | 3600 | 42 | 0.13 | 0.29 | 0.58 |
| 10 | I | 1150 | 3600 | 32 | 0.23 | 0.36 | 0.41 |
| 11 | J | 1190 | 18000 | 22 | 0.40 | 0.43 | 0.17 |
| 12 | H | 1130 | 3100 | 55 | 0.15 | 0.07 | 0.77 |

TABLE II

| | Reaction Conditions | | | Conv. mole % of $CH_4$ fed | Results Fraction of carbon converted, appearing as | | | |
|---|---|---|---|---|---|---|---|---|
| Run No. | Catalyst | Temp. °C. | Sv hr$^{-1}$ | | Yield | Aromatics | Heavy Hydrocarbons | Coke |
| 13 | D | 975 | 12000 | 05 | 67 | 0.0 | 0.87 | 0.07 |
| 14 | D | 1170 | 3174 | 76 | 0 | 0.0 | 0.0 | 1.00 |
| 15 | K | 1100 | 12000 | 25 | 53 | 0.22 | 0.49 | 0.29 |
| 16 | L | 975 | 12000 | 04 | 69 | 0.18 | 0.70 | 0.12 |
| 17 | L | 1179 | 3174 | 73 | 13 | 0.02 | 0.15 | 0.83 |
| 18 | L | 1100 | 12000 | 24 | 58 | 0.21 | 0.54 | 0.25 |
| 19 | A | 976 | 12000 | 01 | 72 | 0.42 | 0.50 | 0.09 |
| 20 | A | 1140 | 3100 | 60 | 17 | 0.04 | 0.18 | 0.79 |
| 21 | A | 1100 | 12000 | 24 | 66 | 0.21 | 0.63 | 0.16 |
| 22 | N | 975 | 12000 | 01 | 65 | 0.40 | 0.42 | 0.18 |
| 23 | N | 1133 | 3100 | 53 | 14 | 0.05 | 0.18 | 0.79 |
| 24 | N | 1097 | 12000 | 22 | 65 | 0.28 | 0.54 | 0.18 |
| 25* | O | 1070 | 12000 | 23 | 64 | 0.14 | 0.69 | 0.17 |

*The feed in this case was 7.5% $H_2$ + 5% $C_2H_6$, balance $CH_4$

Catalysts Used in Tables I & II

In the following catalyst descriptions a "/" is used to indicate that the compound following is a support.

A. $Al_2O_3$: White fused refractory alumina, purchased from Carborundum Company.

B. $ThO_2/Al_2O_3$: A saturated solution of Th(NO$_3$)$_4$.4-H$_2$O in dimethyl formamide was prepared. Forty grams of White fused refractory alumina (Carborundum) in a stainless steel basket were dipped in the above saturated solution of thorium nitrate, and the solvent evaporated in a vacuum oven. After several dippings and dryings the catalyst weight had increased to 43.03 gm. This material was then fired at 1000° F. for 10 hrs. in air, and used in the reactor.

C. $ThO_2$-$Al_2O_3$-$Cs_2O$-$SiO_2$: A solution of 13.6 gm Th(NO$_3$)$_4$.4H$_2$O, 39.4 gm of AlCl$_3$.6H$_2$O and 0.42 gm of Cs(acetate) in 50 ml absolute ethanol was prepared. To this solution 37 ml of Si(EtO)$_4$ was added, followed by 22.5 gm of urea, and 50 ml of propylene oxide. The resulting gel was washed on a Buechner funnel with absolute ethanol until it was the consistency of a stiff paste. This paste was then extruded through a 3/16" die and the resulting extrudate first dried in a vacuum oven, followed by 14 hrs. firing in air at 1650° F.

D. CaO: To 500 ml of distilled H$_2$O were added 55 gm of CaO. The mixture was warmed slightly (to about 60° C.) and stirred, then left to stand overnight. The water was decanted off in the morning and the thick suspension remaining washed with absolute ethanol on a Buechner funnel. The resulting paste was then extruded through a 1/16" die, and the extrudate dried at 140° C., followed by firing at 700° C. for one hour.

E. MgO: This catalyst was purchased from Alfa Products, crushed and the portion passing 10 mesh, but remaining on 12 mesh screen used.

F. $Li_2O/MgO$: Crushed and sized (10/12 mesh) MgO pellets (Alfa) Products were placed in a wire bucket, and dipped in a solution of 18.5 gm $LiNO_3$ in 50 ml warm pyridine. After dipping the pellets were dried in a vacuum oven. Dipping and drying was repeated until the weight increased by 9.4 gm. This material was then fired at 1000° C. for 10 hrs., and kept in a sealed jar until used.

G. $Cr_2O_3-Al_2O_3-Cs_2O$: A solution of 13.06 gm $CrCl_3$, 43.38 gm $AlCl_3$ and 0.42 gm of Cs(acetate) in 315 ml of absolute ethanol was prepared. To cause the $CrCl_3$ to dissolve a small amount (less than 3 gm of $CrCl_2$) was added to the above mixture. To this solution, 250 ml of $H_2O$ were added. After filtering, 115 ml of propylene oxide were added to the aqueous ethanolic solution, followed by sufficient ammonium hydroxide to cause rapid gelling. This gel was then washed with absolute ethanol on a Buechner funnel, and the resulting paste extruded through a 3/16" die. The extrudate was dried overnight in a vacuum oven and then fired in air at 1000° F. for 10 hrs.

H. $ZrO_2-Al_2O_3-SiO_2$: A solution of 53.61 gm $ZrCl_4$ and 11.84 gm $AlCl_3.6H_2O$ in 600 ml of warm absolute ethanol was prepared. After filtering through celite, the filtrate was allowed to cool to room temperature, and 75.75 ml of $(EtO)_4Si$ added and stirred thoroughly. To this clear solution were then added 500 ml of $H_2O$, followed by 105 ml of propylene oxide, with constant stirring. After about 45 minutes, a gel formed. The gel was allowed to stand overnight at room temperature, and was then filtered, and washed repeatedly with absolute ethanol in a large Buechner funnel. The resulting paste was extruded through a 1/16" die and the extrudate dried at 100° C. in a vacuum oven. The dried extrudate was then fired at 800° C. for 12 hrs. It was then sieved to remove fines, and the 10/20 mesh fraction used.

I. $K_2O/Al_2O_3$: To 60 gm of white fused refractory alumina (Carborundum) were added a solution of 0.27 gm of $K_2CO_3$ in 3 ml $H_2O$. The solution was added dropwise with stirring to distribute it uniformly. The mixture was dried in an over at 150° C. for 2 hrs., then fired in a muffle furnace at 800° C. for 17 hrs.

J. SrO/MgO: Strontium nitrate was first prepared by slowly adding 70 gm of $SrCO_3$ to 57 ml of concentrated nitric acid with constant stirring. This mixture was heated 3 hrs. on a hot plate until all $CO_2$ evolution ceased. The wet precipitate formed was collected and placed in a vacuum oven at 100° C. overnight. The resulting $Sr(NO_3)_2$ was a hard white dry crystalline solid. A saturated solution of $Sr(NO_3)_2$ in dimethyl formamide was prepared and 20.4 gm of 10/12 mesh crushed MgO pellets (Alfa) dipped in the dimethylformamide solution, then dried. When 28 gm of $Sr(No_3)_2$ had been deposited, the coated MgO was fired at 1000° F. in air for 4 hrs.

K. $BaO/Al_2O_3$: The support for this catalyst was prepared by crushing and sieving fused white alumina refractory bubbles, obtained from Carborundum Company. Particles in the size range 8 to 12 mesh were used. To 20 gr. of this support was added a solution of 0.6 gr $Ba(NO_3)_2$ in 4 ml of distilled water. The addition was carried out dropwise, with continuous stirring of the support. After drying 3 hrs at 120° C., the catalyst was calcined at 800° C. in air for 3 hrs.

L. $ZrO_2-SiO_2-Al_2O_3$: This catalyst was a low area support purchased from Norton Co., their designation SZ 5245, which was crushed and sieved. Particles in the range 12–20 mesh were used.

N. $ThO_2/Al_2O_3$: Fused white alumina refractory bubbles, obtained from the Carborundum Company were crushed and sieved and the fraction 8–20 mesh used in preparing this catalyst. To 354.5 gr of the crushed and sieved refractory bubbles was added a solution of 43.6 gr $Th(NO_3)_4 \cdot H_2O$ in 70.9 ml of distilled water. Small portions of the solution were added with continuous stirring. The wet slurry was placed in the flask of a Rotovac apparatus, and ammonia vapors passed over the mixture while the flask was rotated. Thorium hydroxide was precipitated on the support by this procedure. Even dispersion was maintained by the flask rotation. The mixture was first dried under a heat lamp in a stream of nitrogen, then calcined in air at 1000° C. for 3 hrs.

O. $(La_2O_3-SrO)/Al_2O_3$: Fused white alumina refractory bubbles, obtained from the Carborundum Company were crushed and sieved, and the particles in the size range 12–20 mesh used. To 20 gr of this material was added a solution of 2.40 gr $La(NO_3)_3 \cdot H_2O$ and 0.6 gr $Sr(NO_3)_2$ in 4 ml of distilled water. The solution was added dropwise with continuous stirring. The wet mixture was then dried in an oven at 200° C. for 2 hrs, and finally calcined for 3 hrs in air at 1000° C.

Examples 1–11, 15, 18, 21, 24 and 25 illustrate various preferred embodiments of the invention using various metal compound-containing catalysts and reaction conditions. All of these examples illustrate that high yields of higher molecular weight hydrocarbons, particularly aromatics, are obtained when using the critical process conditions of the present invention.

Examples 12–14, 16–17, 19–20 and 22–23 are not part of the present invention and were run for comparative purposes using various catalysts from different Groups of the Periodic Table. These examples when compared to the examples falling within the scope of the present invention illustrate the criticality of temperatures greater than 1000° C. and space velocity greater than 3200 $hr^{-1}$ in obtaining high conversions of methane to the desired liquid products.

Comparison of Examples 9 and 12, Table I, illustrates that for a catalyst containing predominantly a Group IVB metal compound that a relatively small change in gas hourly space velocity from 3600 to 3100 $hr^{-1}$ resulted in a dramatic and highly detrimental increase in the tar/coke yield of 33% and that it also had the extremely undesirable effect of decreasing the fraction of the most desired product, i.e. the aromatics, by a factor of 4.

Comparison of Example 13 with 14, Table II, illustrates that for a Group IIA metal compound-containing catalyst that the conversion of methane is unacceptably low at a temperature of 975° C. and the production of coke is unacceptable high at a space velocity of 3174 $hr^{-1}$. Examples 4–6, 11 and 15 illustrate high conversions of methane to the desired products using various Group IIA metal compound-containing catalysts with temperatures greater than 1000° C. and space velocities greater than 3200 hr$^{-1}$.

Comparison of Example 16 with 18, Table II, illustrates that conversion of methane at temperatures below 1000° C. is unacceptably low with a catalyst containing a Group IVB metal compound. Comparison of Example 17 and 18 illustrates the dramatic and unacceptable increase in the production of coke when the space velocity is below 3200 hr$^{-1}$. Examples 8, 9, 12, and 18 illustrate high conversions of methane to the desired products using Group IVB metal compound-containing catalysts with temperatures greater than 1000° C. and space velocities greater than 3200 hr$^{-1}$.

Comparison of Example 19 with 21 illustrates that conversion of methane at temperatures below 1000° C. is unacceptably low with a catalysts which is a Group IIIA metal compound. Comparison of Example 20 and 21 illustrates the dramatic and unacceptable increase in the production of coke when the space velocity is below 3200 hr$^{-1}$. Examples 1 and 21 illustrate high conversions of methane to the desired products using Group IIIA metal-containing catalysts with temperatures greater than 1000° C. and space velocities greater than 3200 hr$^{-1}$.

Comparison of Example 22 with 24 illustrates that conversion of methane at temperatures below 1000° C. is unacceptably low with a supported Actinide Series metal compound-containing catalyst. Comparison of Example 23 and 24 illustrates the dramatic and unacceptable increase in the production of coke when the space velocity is below 3200 hr$^{-1}$. Examples 2, 3, and 24 illustrate high conversions of methane to the desired products using Actinide Series metal compound-containing catalysts with temperatures greater than 1000° C. and space velocities greater than 3200 hr$^{-1}$.

Example 25 illustrates high conversions of methane to the desired products using mixtures of Group IIA and IIIA metal compound-containing catalysts with temperatures greater than 1000° C. and space velocities greater than 3200 hr$^{-1}$.

What is claimed is:

1. A process for the production of higher molecular weight hydrocarbons from lower molecular hydrocarbons comprising the steps of:
    (a) introducing into a reaction zone a lower molecular weight hydrocarbon-containing gas and contacting said gas in said zone with a metal compound-containing catalyst containing a carbide, nitride, boride or oxide of a Group IV-B metal, under $C_2+$ hydrocarbon synthesis conditions such that at least 15 mole percent of the lower molecular weight hydrocarbons in said gas are converted to higher molecular weight hydrocarbons, said conditions including a temperature of greater than 1000° C. and a gas hourly space velocity of greater than 6000 hr$^{-1}$;
    (b) withdrawing from said reaction zone a higher molecular weight hydrocarbon-containing stream.

2. The process of claim 1 wherein said temperature is in the range of 1100° to 1200° C., said space velocity is in the range of greater than 6,000 to 36,000 hr$^{-1}$ and at least 20 mole percent of said lower molecular weight hydrocarbons are converted to higher molecular weight hydrocarbons.

3. The process of claim 2 wherein said reaction zone contains a stationary or fluidized bed of a catalyst.

4. The process of claim 3 wherein said lower molecular weight hydrocarbon is methane.

5. The process of claim 4 wherein said temperature is in the range of 1140° to 1175° C. and said space velocity is in the range of 9,000 to 18,000 hr$^{-1}$.

6. The process of claim 5 wherein 40 or more mole percent of said methane containing hydrocarbon gas is converted to higher molecular weight hydrocarbons.

7. The process of claim 6 wherein said higher molecular weight hydrocarbon stream is rich in ethylene or aromatics or both.

8. A process for the production of higher molecular weight hydrocarbons from methane comprising the steps of:
    (a) introducing into a reaction zone a methane-containing gas and contacting said gas in said zone with a catalyst containing a carbide, nitride, boride or oxide of a Group IV-B metal selected from titanium, zirconium or hafnium under $C_2+$ hydrocarbon synthesis conditions such that at least 20 mole percent of said methane in said gas is converted to higher molecular weight hydrocarbons, said conditions including a temperature in the range of 1100° to 1200° C. and a gas hourly space velocity of 6,000 to 36,000 hr$^{-1}$; and
    (b) withdrawing from said reaction zone a higher molecular weight hydrocarbon-containing stream, wherein the carbon-containing reaction products in said stream comprises greater than 90 mole percent higher molecular weight hydrocarbons.

9. The process of claim 8 wherein at least 20 mole percent of said lower molecular weight hydrocarbons are converted to higher molecular weight hydrocarbons.

10. The process of claim 9 wherein said reaction zone contains a stationary or fluidized bed of a catalyst.

11. The process of claim 10 wherein said lower molecular weight hydrocarbon is methane.

12. The process of claim 11 wherein said temperature is in the range of 1140° to 1175° C. and said space velocity is in the range of 9,000 to 18,000 hr$^{-1}$.

13. The process of claim 12 wherein 40 or more mole percent of said methane containing hydrocarbon gas is converted to higher molecular weight hydrocarbons.

14. The process of claim 13 wherein said higher molecular weight hydrocarbon stream is rich in ethylene or aromatics or both.

15. A process for the production of higher molecular weight hydrocarbons from methane comprising the steps of:
    (a) introducing into a reaction zone a methane-containing gas and contacting said gas in said zone with a catalyst containing a zirconium oxide under $C_2+$ hydrocarbon synthesis conditions such that at least 20 mole percent of said methane in said gas is converted to higher molecular weight hydrocarbons, said conditions including a temperature in the range of 1100° to 1200° C. and a gas hourly space velocity of 6,000 to 36,000 hr$^{-1}$; and
    (b) withdrawing from said reaction zone a higher molecular weight hydrocarbon-containing stream, wherein the carbon-containing reaction products in said stream comprises greater than 80 mole percent higher molecular weight hydrocarbons.

* * * * *